(12) United States Patent
Shih

(10) Patent No.: US 6,664,356 B1
(45) Date of Patent: Dec. 16, 2003

(54) LEACH RESISTANT OIL BASED CARRIER FOR COSMETICALLY AND PHARMACEUTICALLY ACTIVE AGENTS

(75) Inventor: Jenn S. Shih, Paramus, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 10/350,404

(22) Filed: Jan. 23, 2003

(51) Int. Cl.[7] ............................................. C08F 220/10
(52) U.S. Cl. .................... 526/328.5; 526/213; 526/265; 526/303.1; 526/307.2; 526/307.6; 526/317.1; 526/319; 526/329.2; 526/333; 424/78.22; 424/78.24
(58) Field of Search ................................ 526/213, 265, 526/303.1, 307.2, 307.6, 317.1, 319, 328.5, 329.2, 333; 424/78.22, 78.24

(56) References Cited

U.S. PATENT DOCUMENTS

| | | | | |
|---|---|---|---|---|
| 5,916,548 | A | * 6/1999 | Hutchins et al. | ......... 424/70.12 |
| 6,255,421 | B1 | * 7/2001 | Plochocka et al. | .......... 526/194 |
| 6,300,442 | B1 | * 10/2001 | Plochocka et al. | .......... 526/194 |
| 2001/0055599 | A1 | * 12/2001 | Drzewiecki et al. | ........ 424/401 |

* cited by examiner

*Primary Examiner*—Helen L. Pezzuto
(74) *Attorney, Agent, or Firm*—Marilyn J. Maue; William J. Davis; Walter Katz

(57) ABSTRACT

This invention relates to a non-leachable, oil based carrier derived from the anhydrous free radical solution polymerization of a water insoluble acrylate and/or acrylamide monomer in an oil medium for use in long lasting skin lubricating formulations.

17 Claims, No Drawings

LEACH RESISTANT OIL BASED CARRIER FOR COSMETICALLY AND PHARMACEUTICALLY ACTIVE AGENTS

BACKGROUND OF THE INVENTION

Oil based formulations for active personal care and pharmaceutical products have certain desirable properties in that they are non-drying, skin friendly compositions which can be derived from materials that are readily available and inexpensive to produce. However, while current carriers, described in U.S. Pat. Nos. 5,015,708; 6,177,068; 6,255,421; 6,255,422 and 6,300,442, are produced by polymerization of monomers in an oil base, the monomeric materials employed are not inherently water insoluble, hence their polymeric products are prone to leaching under extended exposure to high humidity or water environments. This shortcoming is particularly undesirable in carriers employed for suntan or UV blocking formulations. Further, such leachable carriers may be harmful for topically applied pharmaceuticals since the concentration of the active material in the formulation may become harmfully elevated.

Accordingly, it is an object of this invention to provide a water leach-resistant carrier which is compatible with a wide variety of active chemicals and which is inexpensive and easily produced.

Other advantages of the present invention will become apparent from the following description and disclosure.

SUMMARY OF THE INVENTION

In accordance with this invention there is provided a leach resistant carrier composition for active cosmetic and pharmaceutical formulations which comprises, an exclusively water insoluble polymer or polymer mixture including a water insoluble acrylate and/or a water insoluble acrylamide polymer dissolved in oil and derived from the anhydrous, free radical initiated solution polymerization of a corresponding water insoluble monomer or monomers in an oil base or solvent. For the purpose of this invention, the term "acrylate" is intended to include both acrylates and methacrylates and is referred to herein as (meth)acrylate. Similarly, "acrylamide" is intended to include acrylamides and methacrylamides and is indicated herein as (meth)acrylamide.

DETAILED DESCRIPTION OF THE INVENTION

In the preparation of the present polymer carrier compositions, it is essential that the oil during monomer polymerization and in the polymerized product be maintained at between 40 and 90 wt. %, preferably at least equal portions of polymer and oil and most preferably an excess of oil in the range of from 60 to 70 wt. %. At oil concentrations below 40 wt. %, the product is too viscous for easy formulation with active or other components. It is equally important to monitor the initiator feed continuously or in increments throughout the reaction so as to maintain a concentration of from about 0.1 to about 10 wt. %, preferably from 0.2 to 5 wt. % with respect to monomer present in the reactor.

In general, the polymerization is effected under a blanket of nitrogen at a temperature of between about 50° and about 150° C. with agitation over a period of from about 2 to about 25 hours.

The monomeric components, from which the present polymers are derived, are exclusively water insoluble monomers selected from the group consisting essentially of a $C_8$ to $C_{30}$ alkyl substituted (meth)acrylate; a N—$C_8$ to $C_{30}$ alkyl (meth)acrylamide; a $C_1$ to $C_6$ alkyl (meth)acrylate; a N—$C_1$ to $C_6$ alkyl (meth)acrylamide and mixtures thereof. The monomeric mixture may optionally include up to 50 wt. %, preferably not more than 25 wt. %, of another water insoluble monomer such as, styrene, vinyl chloride, 2-vinyl pyridine, 4-vinyl pyridine, an ethylenically unsaturated ester, for example a $C_6$ to $C_{18}$ alkyl-cinnamate, -maleate or -crotonate and the like; as well as up to 10 wt. % of a water soluble polymerizable monomer such as, for example, vinyl amide, vinylpyrrolidone, vinyl caprolactam, hydroxyalkyl (meth)acrylate, (meth)acrylic acid, cinnamic acid, N,N-dimethylamoniethyl methacrylate, N,N-dimethylaminopropyl (meth)acrylamide and mixtures of the foregoing monomers. Such optional monomers can be added to neutralize the monomeric component to a pH of about 7 in a subsequent formulation which will assure stability of an o/w emulsion.

The monomer component may also include up to 5 wt. % of a crosslinking agent. Suitable crosslinking agents include, but are not limited to, diallylimidolidone, the divinyl ether of diethylene glycol, pentaerythritol triallyl ether (PETA), triallyl-1,3,5-triazin-2,4,6-(1H, 3H, 5H)trione (TATT), ethylene glycol diacrylate, 2,4,6-triallyloxy-1,3,5-triazine, N-vinyl-3-(E)-ethylidenepyrrolidone (EVP), 1,7-octadiene, 1,9-decadiene, divinyl benzene, methylene-bis (methacrylamide) methylene-bis(acrylamide), N,N-divinylimidazolidone, ethylidene-bis(N-vinylpyrrolidone) (EBVP) and bis(N,N-acrylamide) and mixtures thereof.

The above optional monomers can be added to neutralize the monomeric mixture to pH of about 7 in the formulation which may improve the stability of an o/w emulsion.

The preferred monomer is a mixture of long and short chain (meth)acrylates and/or (meth)acrylamides, particularly mixtures of acrylates and methacrylates.

The oil base of the present composition contains a cosmetically or pharmaceutically acceptable, non-volatile, water repellant material having a viscosity of from about 5 to about 600,000 centistokes, preferably from about 10 to about 300 centistokes, at 25° C. Representative examples of suitable bases include individual oils or mixtures which include light and heavy mineral oils, silicone oils, plant and animal oils and water insoluble esters such as esters, e.g. the isocetyloleate, stearyl laurate, isopropyl adipate, isopropyl myristate or isocetyl stearate and mixtures thereof. The oil base may contain up to 15 wt. %, more often from 5 to 10 wt. %, of a glycol such as propylene glycol, pentanediol, methyl-pentanediol and mixtures of such.

Suitable siloxane oils are selected from non-volatile silicones, such as polyalkyl siloxanes, polyaryl siloxanes, polyalkylaryl siloxanes and polyether siloxane copolymers; and volatile silicones such as cyclomethicones also may be used.

Non-volatile polyalkylsiloxanes thus include, for example, polydimethylsiloxanes (Dimethicone) with viscosities ranging from about 5 to about 600,000 centistokes (cS) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued Jul. 20, 1970. Preferably, the viscosity of these siloxanes selected have a viscosity of about 100 to about 100,000 cS, and most preferably, a viscosity of up to about 15,000 cS.

Suitable non-volatile polyalkylaryl siloxanes include, for example, poly(methylphenyl) siloxanes having viscosities of about 15 to 65 cS at 25° C. These siloxanes are available, for example, from the General Electric as SF 1075 methylphenyl fluid or from Dow Corning as 556 Cosmetic Grade Fluid. Additionally, poly(dimethylsiloxane)-(diphenylsiloxane) copolymers having a viscosity in the range of about 10 to 100,000 cS at 25° C. are useful.

These and other suitable silicones are disclosed in U.S. Pat. Nos. 2,826,551, 3,964,500 and 4,364,837.

The polymerization process is carried out in the monitored presence of a free radical initiator. Suitable free radical initiators are peroxy esters, peroxide, percarbonates and azo compounds including diacetyl peroxide, dibenzoyl peroxide, dilauroyl peroxide, t-butyl peroxypivalate, t-butyl peroctoate, t-amyl peroxypivalate, t-butyl peroxy-2-ethylhexanoate, di-(4-t-butylcyclohexyl)peroxydicarbonate, 2,2'-azo-bis(isobutyronitrile), 2,2'-azo-bis(2,4-dimethylvaleronitrile), or 1,1'-azo-bis(cyanocyclohexane), and mixtures thereof.

Having generally described the invention, reference is had to the following examples which illustrate preferred embodiments but which are not to be construed as limiting to the scope of the invention as set forth in the accompanying claims.

EXAMPLE 1

Into a 1-liter, 4-necked glass kettle, equipped with two feeding pumps, an anchor agitator, a thermocouple and a condenser, was introduced 300 g of mineral oil, 35 g of methyl methacrylate, 70 g of butyl acrylate and 45 g of stearyl methacrylate. The solution was purged with nitrogen throughout the ensuing process. The resulting solution was heated to 65° C. and held at that temperature under agitation for 30 minutes, after which 0.5 g of t-butylperoxy pivalate was gradually stirred into the solution which was held at 65° C. for 5 additional hours. The temperature was then raised to 90° C. and 0.2 g of t-butylperoxy pivalate was added every 2 hours over a 10 hour period. The solution was then held for an additional 2 hours before cooling to room temperature and recovered as a clear polymer in oil solution suitable for use as the skin friendly, leach-resistant carrier for a cosmetic or pharmaceutical formulation.

EXAMPLE 2

The general procedure of Example 1 was repeated except that a 200 ml glass jar replaced the kettle and the monomer charged consisted of 2.5 g of methyl methacrylate, 6.12 g of butyl acrylate, 3.9 g of stearyl methacrylate and 50 g of isocetyl stearate. In this example, the solution polymerization was carried out at 70° C. and 0.1 g of t-butyl peroxy pivalate was added. The resulting clear polymer in oil solution was a suitable oil carrier product similar to that obtained in Example 1.

Repeating the above experiment in the absence of non-volatile mineral oil and substituting an aqueous solution of glycerol as the polymerization medium, resulted in a homogeneous water leachable suspension not suitable as a water insoluble carrier.

EXAMPLE 3

The general procedure of Example 1 was again repeated except that the charge to the kettle consisted of 300 g of mineral oil, 35 g of methyl methacrylate, 70 g of butyl acrylate, 40 g of stearyl methacrylate and 5 g of acrylic acid.

In this example, the monomer and t-butylpeoxy pivalate initiator charged to the reactor was held for one hour before raising the temperature to 130° C. Thereafter, 0.2 g of di-t-butyl peroxide was added every 6 hours over a 12 hour period and then held for an additional 4 hours. The clear polymer in oil solution recovered was a leach-resistant solution suitable as a skin friendly, water insoluble carrier for a cosmetic or pharmaceutical formulation.

Representative formulations employing the present oil based carrier include the following.

| WATERPROOF SUNSCREEN SPRAY MIST | |
|---|---|
| Ingredients: | % Wt. |
| Phase A | |
| Anhydrous ethanol | 62.20 |
| Deionized water | q.s. |
| Phase B | |
| Carrier of Example 1 | 3.00 |
| octyl methoxycinnamate | 7.50 |
| benzophenone-3 | 3.00 |
| methyl anthranilate | 3.50 |
| caprylyl methicone | 5.00 |
| $C_{12-15}$ alkyl benzoate | 10.00 |
| butylated hydroxytoluene | 0.02 |
| propylparaben | 0.10 |
| Vitamin E | 0.25 |
| Phase C | |
| Fragrance | 0.50 |

Procedure: The ingredients in phase B are added to phase A one by one and mixed until a clear composition is obtained, after which fragrance is added and mixing repeated until clear.

| SUN SCREEN SPRAY | |
|---|---|
| Ingredients: | % Wt. |
| Phase A | |
| Ceralution H (Condea Vista) | 0.5 |
| isotrideceth-12 | 0.5 |
| caprylic/capric triglyceride | 3.3 |
| $C_{1-15}$ alkylbenzoate | 3.6 |
| Cyclomethicone | 2.5 |
| Carrier of Example 2 | 3.0 |
| Octylsalicylate | 3.0 |
| Octyl methoxycinnamate | 7.0 |
| Butyl methoxydibenzoylmethane | 0.5 |
| Phase B | |
| Deionized $H_2O$ | 13.0 |
| Ceralution F (Condea Vista) | 1.0 |
| Xanthan gum | 0.2 |
| Glycerin | 5.0 |
| Phase C | |
| Deionized $H_2O$ | 48.9 |
| Alcohol (Ethanol) | 8.0 |
| Benzophenone-3 | 1.0 |
| Fragrance | 0.6 |

Procedure: Phases A and B are separately heated to 60° C. and then combined to provide a 200 g mixture. The mixture was homogenized with a kitchen homogenizer for about 2 minutes or until droplet random movement and droplet size of less than 1 um is achieved. Phase C is then added and homogenized for 2 minutes. The resulting mixture is the cooled and de-aerated to provide a clear spray.

LONG WEARING WATER-RESISTANT MASCARA

| Ingredients: | % Wt. |
|---|---|
| Phase A | |
| Oil based Carrier of Example 1 | 5.20 |
| Isooctane | 7.80 |
| White beeswax | 4.00 |
| Ozokerite 170D | 8.00 |
| Stearic acid | 5.00 |
| Phase B | |
| Water | 58.04 |
| Black iron oxide | 10.00 |
| Hydroxyethylcellulose | 0.20 |
| PVP K-30 | 1.00 |
| Methylparaben | 0.10 |
| Triethanolamine | 0.66 |

Procedure: The carrier of example 1 was dissolved in isooctane and heated to 85° C., after which the remaining ingredients of phase A were added with constant mixing. The ingredients of phase B were separately heated to 85° C. and mixed. Phase A was then slowly added to phase B and homogenized with a high shear mixer. After about 3 minutes, the mixture was cooled and gently stirred to produce a flake-, smudge- and water-resistant mascara fluid.

WATER RESISTANT MASCARA

| Ingredients: | % Wt. |
|---|---|
| Phase A | |
| Stearic acid | 5.00 |
| White beeswax | 7.50 |
| Ozokerite 170D | 7.50 |
| Black iron oxide | 10.00 |
| Phase B | |
| Oil based Carrier of Example 1 | 4.00 |
| Ethanol, 200 proof | 6.00 |
| Phase C | |
| Water | 56.35 |
| Triethanolamine | 1.30 |
| Hydroxyethylcellulose | 0.25 |
| PVP K-30 | 2.00 |
| Methylparaben | 0.10 |

Procedure: The ingredients of phase A were mixed at 65° C. The ingredients of Phase B and phase C were separately mixed at 50° C. and phase B was slowly added to phase C under moderate mixing for 30 minutes with a homogenizer and the temperature raised to 65° C. The combined phases B and C were then homogenized with phase A to provide the mascara emulsion.

OIL-IN-WATER SUN CREAM

| Ingredients | % Wt. |
|---|---|
| Phase A | |
| octyl methoxycinnamate | 4.00 |
| butyl methoxydibenzoylmethane | 1.50 |

-continued

OIL-IN-WATER SUN CREAM

| Ingredients | % Wt. |
|---|---|
| Oil based Carrier of Example 3 | 5.00 |
| caprylic/capric triglyceride | 3.00 |
| Sepicide HB (Seppic) (phenoxyethanol (and) methylparaben (and) ethylparaben (and) propylparaben (and) butylparaben) | 0.50 |
| potassium cetyl phosphate | 2.00 |
| Phase B | |
| Deionized water | 72.15 |
| Carbopol 980 (BF Goodrich) | 0.10 |
| Propylene glycol | 3.50 |
| disodium salt of ethylene diamine tetra acetic acid | 0.10 |
| Phase C | |
| Potassium hydroxide (10%) | 0.15 |
| Dow Corning 245 Fluid (cyclopentasiloxane) | 4.00 |
| Dow corning 9040 Silicone Elastomer Blend (cyclopentasiloxane (and) dimethicone crosspolymer (and) cyclohexasiloxane) | 4.00 |

Procedure: At 85° C. the first five ingredients of phase A were stirred until a uniform mixture was obtained, after which potassium cetyl phosphate was added and mixed at the same temperature. In a separate vessel, carbomer was dispersed in water at 75° C. and polypropylene glycol and EDTA were added and then neutralized with potassium hydroxide to a pH of 7. The neutralized mixture at 75° C. was added to phase A under strong agitation and mixing continued while cooling to 40° C. The separate mixture of cyclopentasiloxane and the elastomer blend as phase C was then added to combined phases A and B at pH 7, under strong agitation while cooling. After adjustment with water to compensate for that lost during heating, the resulting liquid formulation is introduced into an aerosol spray can.

The foregoing examples and formulations represent specific examples of preferred embodiments; however, it will be understood that many modifications and substitutions can be made in the above without departing from the scope of this invention.

What is claimed is:

1. A glycerol-free, water resistant oil soluble carrier for a cosmetically or pharmaceutically active agent which comprises an exclusively water insoluble polymer mixture derived from a long chain and a short chain alkyl (meth) acrylate and/or an alkyl (meth)acrylamide, said polymer dissolved in a cosmetically or pharmaceutically acceptable, non-volatile, water insoluble oil having a viscosity between about 5 and about 600,000 centistokes at 25° C.

2. The carrier of claim 1 wherein said oil has a viscosity of between about 10 and about 300 centistokes at 25° C.

3. The carrier of claim 1 wherein said oil is selected from the group consisting of a mineral, plant, animal oil, a silicone oil, isocetyl oleate, stearyl laurate, isopropyl adipate, isopropyl myristate, isocetyl stearate and mixyutes thereof.

4. The carrier of claim 3 wherein said oil is a isocetyl oleate, stearyl laurate, isopropyl adipate, iso propyl myristate, isocetyl stearate or a mixture thereof.

5. The carrier of claim 1 wherein said long chain polymer is a polymer of a monomer selected from the group consisting of a $C_8$ to $C_{30}$ alkyl (meth)acrylate, an N—$C_8$ to $C_{30}$ alkyl (meth)acrylamide and a mixture thereof.

6. The carrier of claim 1 wherein said short chain polymer is a polymer of a monomer selected from the group consisting of a $C_1$ to $C_6$ alkyl (meth)acrylate, a $C_1$ to $C_6$ alkyl (meth)acrylamide and a mixture thereof.

7. The carrier of claim 1 wherein said polymer mixture optionally contains up to 50% of a polymer of a water insoluble monomer selected from the group consisting of styrene, vinyl chloride, a vinyl pyridine, a $C_6$ to $C_{18}$ alkyl-cinnamate, -crotonate or -maleate and a mixture thereof.

8. The carrier of claim 1 wherein said polymer mixture optionally contains up to 10% of a neutralizing agent derived from a polymerizable acid or base selected from the group consisting of (methacrylic acid, cinnamic acid, dimethylamino $C_1$ to $C_2$ alkyl (meth)acrylate and N,N-dimethylamino $C_1$ to $C_2$ alkyl (meth)acrylamide.

9. The carrier of claim 1 wherein the oil content is at least 50% of the carrier.

10. The carrier of claim 1 wherein the oil content is between 60 and 70% of the carrier.

11. The carrier of claim 1 wherein the oil optionally contains up to 15 wt. % glycol.

12. The carrier of claim 11 wherein the oil contains between about 5 and about 10% glycol.

13. The carrier of claim 11 wherein the glycol is selected from the group consisting of propylene glycol, pentanediol, 2-methyl pentanediol and mixtures thereof.

14. The carrier of claim 1 wherein said polymer is optionally crosslinked with up to 5 wt. % of a crosslinking agent.

15. A process of making the carrier of claim 1 in a solution polymerization which comprises under anhydrous conditions, heating a reaction mixture of from 10 to 60 wt. % of said water insoluble monomer in from 40 to 90 wt. % of said oil to form a solution; adding a free radical initiator to initiate the solution polymerization; maintaining the concentration of initiator between 0.1 and 10 wt. % and the concentration of oil at 40 to 90 wt. % throughout the polymerization reaction.

16. A cosmetic or pharmaceutical product containing an active cosmetic or pharmaceutical agent and the oil based carrier of claim 1.

17. A sun block lotion containing an active sun blocking agent and a carrier therefore which is the oil based carrier of claim 1.

* * * * *